US008520799B2

(12) United States Patent
Nagai et al.

(10) Patent No.: US 8,520,799 B2
(45) Date of Patent: Aug. 27, 2013

(54) ANALYSIS METHOD, RADIATION IMAGING APPARATUS USING ANALYSIS METHOD, AND ANALYSIS PROGRAM FOR EXECUTING ANALYSIS METHOD

(75) Inventors: Kentaro Nagai, Yokohama (JP); Toru Den, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 270 days.

(21) Appl. No.: 13/060,112

(22) PCT Filed: Oct. 28, 2009

(86) PCT No.: PCT/JP2009/068863
§ 371 (c)(1),
(2), (4) Date: Feb. 22, 2011

(87) PCT Pub. No.: WO2010/050611
PCT Pub. Date: May 6, 2010

(65) Prior Publication Data
US 2011/0158493 A1      Jun. 30, 2011

(30) Foreign Application Priority Data

Oct. 29, 2008   (JP) ................................. 2008-278425

(51) Int. Cl.
*G03H 5/00*         (2006.01)
(52) U.S. Cl.
USPC .......................................................... 378/36
(58) Field of Classification Search
USPC ............................... 378/36, 62; 382/128–131
See application file for complete search history.

(56) References Cited

U.S. PATENT DOCUMENTS
5,424,743 A      6/1995   Ghiglia et al. .............. 342/25 C

OTHER PUBLICATIONS

M.Takeda et al., "Fourier-Transform Method of Fringe-Pattern Analysis for Computer-Based Topography and Interferometry", *J. Opt. Soc. Am.*, vol. 72, No. 1, pp. 156-160 (Jan. 1982).
E. Zappa et al., "Comparison of Eight Unwrapping Algorithms Applied to Fourier-Transform Profilometry", *Optics and Lasers in Engineering*, Elsevier, vol. 46, No. 2, pp. 106-116 (Oct. 24, 2007), XP022342808, ISBN: 0143-8166.
Y. Lu et al., "Weighted Least-Squares Phase Unwrapping Algorithm Based on Derivative Variance Correlation Map", *Opti Wissenschaftliche Verlag Gmbh.* Stuttgart, vol. 118, No. 2, pp. 62-66 (Jan. 3, 2007), XP005822798, ISBN: 0030-4026.
D.C. Ghiglia et al., "Minimum LP-Norm Two-Dimensional Phase Unwrapping", *J. Opt. Soc. Am. A*, vol. 13, No. 10, pp. 1999-2013 (Oct. 1996).

*Primary Examiner* — Courtney Thomas
(74) *Attorney, Agent, or Firm* — Fitzpatrick, Cella, Harper & Scinto (57) ABSTRACT

An analysis method for use in a radiation imaging apparatus employing intensity information of interference fringes of radiation rays that have passed through a detected object includes the steps of generating first phase information of the detected object wrapped into a range of $2\pi$ from the intensity information of the interference fringes; generating information on an absorption intensity gradient of the detected object from the intensity information of the interference fringes; generating a weighting function on the basis of an absolute value of a gradient in the information on the absorption intensity gradient; and generating second phase information by unwrapping the first phase information by using the weighting function.

14 Claims, 9 Drawing Sheets

ANALYSIS METHOD, RADIATION IMAGING APPARATUS USING ANALYSIS METHOD, AND ANALYSIS PROGRAM FOR EXECUTING ANALYSIS METHOD

TECHNICAL FIELD

The present invention relates to an analysis method, a radiation imaging apparatus using the analysis method, and an analysis program for executing the analysis method.

BACKGROUND ART

X-rays, which are an example of radiation rays, are used in imaging methods in areas of industry, such as non-destructive inspection of the inside of materials, in areas of medical images, such as X-ray photography and X-ray computed tomography (CT), and in other areas. Examples of imaging methods employing X-rays include an absorption contrast method and a phase contrast method.

In the absorption contrast method, an image of a detected object can be obtained by producing an absorption contrast on the basis of the attenuation in X-rays caused when the X-rays pass through the detected object.

Meanwhile, in the phase contrast method, an image of a detected object can be obtained by producing a phase contrast on the basis of a phase change caused when X-rays pass through the detected object. This technique is called X-ray phase imaging. Since X-ray phase imaging achieves an excellent sensitivity with respect to biological soft tissues composed of light elements, application to medical images has been expected.

In the process of analysis, information on a phase change obtained by X-ray phase imaging is wrapped into the range of $2\pi$. Thus, it is necessary to obtain the true phase by unwrapping the wrapped phase to acquire a reconstructed phase image. However, since the phase changes greatly in an edge portion of a detected object, information on the wrapped phase includes a phase jump, that is, a portion in which the phase changes discontinuously. When phase information including such a portion in which the phase changes discontinuously is unwrapped, a problem may occur in which an inconsistency occurs between the portion in which the phase changes discontinuously and a portion in which the phase changes continuously and thus distortion which originally does not exist appears.

Under the circumstances described above, a method for performing unwrapping by carrying out iterative calculations using a least-squares method is disclosed in Non-Patent Citation 1. A method for performing a least-squares method using a weighting function in order to minimize distortion even in a case where a portion in which the phase changes discontinuously exists is also disclosed in Non-Patent Citation 1. The "weighting function" is a function for giving, when unwrapping is performed, different weights to a portion in which the phase changes discontinuously and a portion in which the phase changes continuously. With the use of a weighting function, an image having less distortion can be obtained.

A specific unwrapping method disclosed in Non-Patent Citation 1 is performed as follows:
(i) Wrapped phase information is obtained.
(ii) A tentative true phase value is determined and a weighting function is set on the basis of the determined true phase value.
(iii) An optimal true phase value (first value) is calculated using a least-squares method on the basis of the weighting function set in (ii). That is, the true phase value that is obtained when the sum of squares of residuals is minimum is calculated.
(iv) The weighting function is reset on the basis of the optimal true phase value (first value) calculated in (iii).
(v) An optimal true phase value (second value) is calculated using the least-squares method on the basis of the weighting function set in (iv).
(vi) A more accurate weighting function is obtained and a more accurate true phase value is calculated by performing the above-mentioned calculations repeatedly until the sum of squares of residuals converges to a certain value.

The calculation method described above has a problem in that since iterative calculations are performed while a weighting function and a true phase value are corrected alternately, a long time is required for obtaining an accurate true phase value.

In contrast, when the number of iterative calculations decreases, a weighting function can be obtained quickly and the true phase value can thus be obtained quickly. However, it is difficult to obtain an accurate weighting function and an accurate true phase value.

Non-Patent Citation 1

Dennis C. Ghiglia and Louis A. Romero, *J. Opt. Soc. Am. A*, Vol. 13, No. 10 (1996)

DISCLOSURE OF INVENTION

The present invention provides a method for generating an accurate weighting function quickly and simply and performing unwrapping quickly compared with Non-Patent Citation 1.

An analysis method according to an aspect of the present invention for use in a radiation imaging apparatus employing intensity information of interference fringes of radiation rays that have passed through a detected object, includes the steps of generating first phase information of the detected object wrapped into a range of $2\pi$ from the intensity information of the interference fringes; generating information on an absorption intensity gradient of the detected object from the intensity information of the interference fringes; generating a weighting function on the basis of an absolute value of a gradient in the information on the absorption intensity gradient; and generating second phase information by unwrapping the first phase information by using the weighting function.

A radiation imaging apparatus according to another aspect of the present invention includes a radiation generator; a phase grating configured to shift a phase of radiation rays generated by the radiation generator; an absorption grating configured to enhance a self-image formed when the radiation rays pass through the phase grating and a detected object; a detector configured to detect intensity information of interference fringes of the radiation rays that have passed through the absorption grating; and an operation unit configured to perform an operation for obtaining an image of the detected object from the intensity information of the interference fringes detected by the detector. The operation performed by the operation unit includes the steps of generating first phase information of the detected object wrapped into a range of $2\pi$ from the intensity information of the interference fringes, generating information on an absorption intensity gradient of the detected object from the intensity information of the interference fringes, generating a weighting function on the basis of an absolute value of a gradient in the information on the absorption intensity gradient, and generating second phase information by unwrapping the first phase information by using the weighting function.

An analysis program according to still another aspect of the present invention for use in a radiation imaging apparatus employing intensity information of interference fringes of radiation rays that have passed through a detected object, causes a central processing unit to execute processing including the steps of generating first phase information of the detected object wrapped into a range of $2\pi$ from the intensity information of the interference fringes; generating information on an absorption intensity gradient of the detected object from the intensity information of the interference fringes; generating a weighting function on the basis of an absolute value of a gradient in the information on the absorption intensity gradient; and generating second phase information by unwrapping the first phase information by using the weighting function.

According to an aspect of the present invention, since an accurate weighting function can be generated quickly and simply, unwrapping can be performed quickly and simply, compared with Non-Patent Citation 1.

DESCRIPTION OF EMBODIMENTS

An example of an analysis method according to an embodiment of the present invention for use in a radiation imaging apparatus employing intensity information of interference fringes produced by radiation will be explained.

Figure 1:
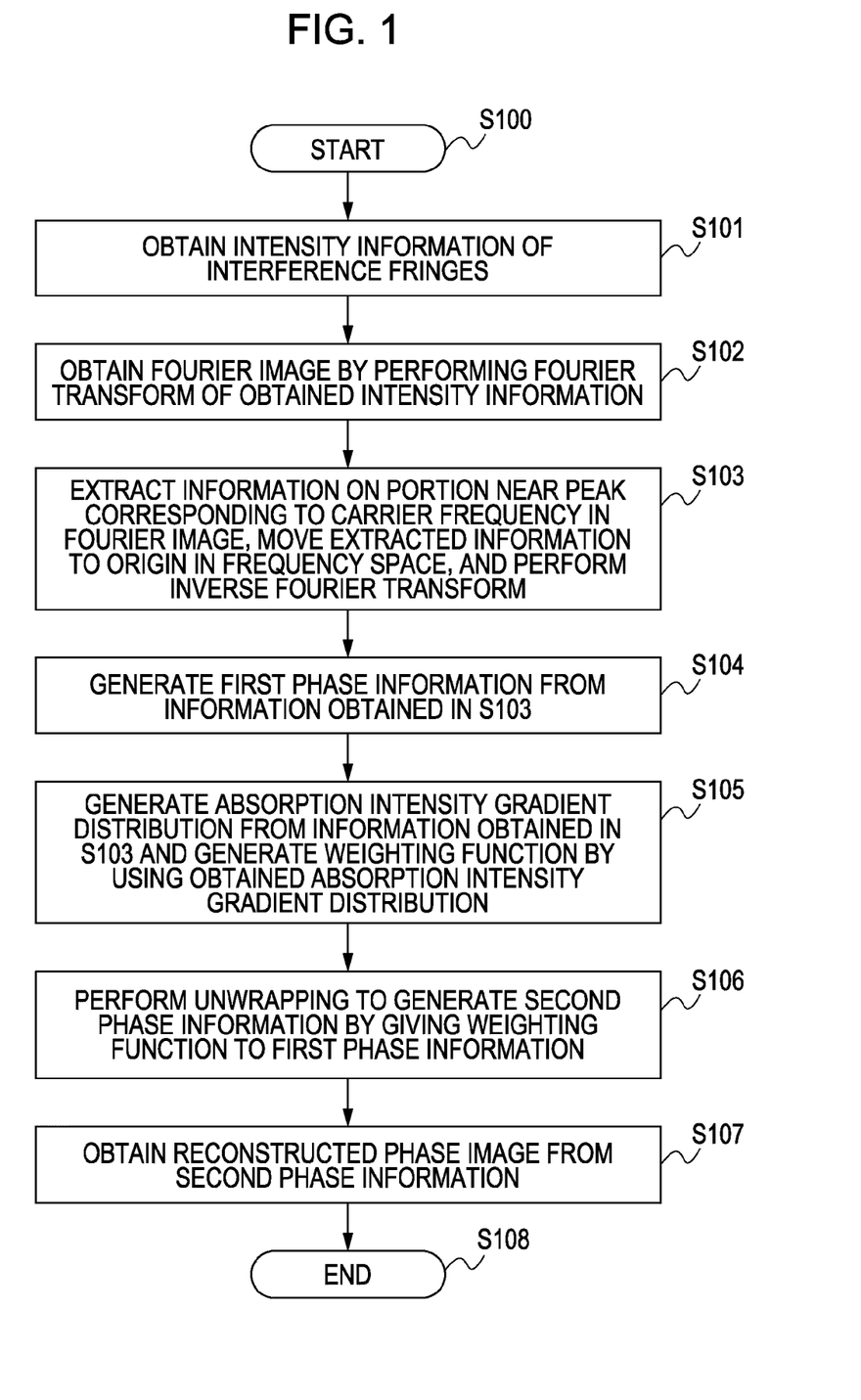
FIG. 1 illustrates an example of a flowchart of an analysis method according to an embodiment of the present invention.

FIG. 1 is a flowchart showing a process from acquisition of intensity information of interference fringes to acquisition of a reconstructed phase image. Steps of the flowchart shown in FIG. 1 will be explained in order.

In step S101, intensity information of interference fringes is obtained. Here, "intensity information of interference fringes" means information describing the properties, such as pattern and brightness, of interference fringes caused by interference being produced by radiation using an interferometer or the like. In addition, "radiation" means radiation rays, in a broad sense, including X-rays, $\alpha$-rays, $\beta$-rays, $\gamma$-rays, ultraviolet rays, corpuscular rays such as electron rays, and electromagnetic waves. It is desirable that X-rays, which realize transmission and absorption at the same time, be used as radiation rays. In addition, it is desirable to use X-rays having a wavelength within a range from about 0.1 Å to about 5 Å that realize absorption to some extent rather than X-rays having an extremely short wavelength. In a case where an object to be detected has both the properties of transmission and absorption with respect to a wavelength range, coherent electromagnetic waves such as laser beams may be used. X-rays to be applied are not necessarily completely coherent. The X-rays only need to have a coherence length at which interference occurs. For example, in the case of a Talbot interferometer, interference occurs at a coherence length that is longer than the pitch of a grating used.

Intensity information of detected interference fringes is represented using equation (1):

$$g(x,y)=a(x,y)+b(x,y)\cos(2\pi f_0 x+\phi'(x,y)) \quad (1)$$

In equation (1), "$a(x,y)$" represents the background, which is not related to the pattern of interference fringes, and "$b(x,y)$" represents the brightness of interference fringes. In addition, "$f_0$" represents the carrier frequency of interference fringes, and "$\phi'(x,y)$" represents a phase change occurring when radiation rays pass through a detected object. The carrier frequency $f_0$ is a parameter that is determined in accordance with the grating pitch of a diffraction grating used when interference fringes are produced.

Equation (1) can be transformed to equation (2):

$$g(x,y)=a(x,y)+c(x,y)\exp(2\pi i f_0 x)+c^*(x,y)\exp(-2\pi i f_0 x) \quad (2)$$

In equation (2), "$c(x,y)$" is represented using equation (3):

$$c(x,y)=\tfrac{1}{2}b(x,y)\exp[i\phi'(x,y)] \quad (3)$$

Here, equation (3) only includes information relating to a phase. Equation (3) is extended to an equation including information on absorption. That is, equation (4), in which "$\psi(x,y)$" represents an absorption intensity gradient, is obtained:

$$c(x,y)=1/2b_0\exp[i(\phi'(x,y)+i\phi(x,y))] \quad (4).$$

In equation (4), the relationship between "$\phi(x,y)$" and "$b(x,y)$" can be represented using equation (5):

$$b(x,y)=b_0\exp(-\psi(x,y)) \quad (5)$$

In equation (5), "$b_0$" represents a constant.

In step S102, a Fourier transform, which is described, for example, in Mitsuo Takeda et al., J. Opt. Soc. Am., Vol. 72, No. 1 (1982), is performed on equation (2), and equation (6) is obtained:

$$G(f_x,f_y)=A(f_x,f_y)+C(f_x-f_0,f_y)+C^*(f_x+f_0,f_y) \quad (6)$$

Figure 2:
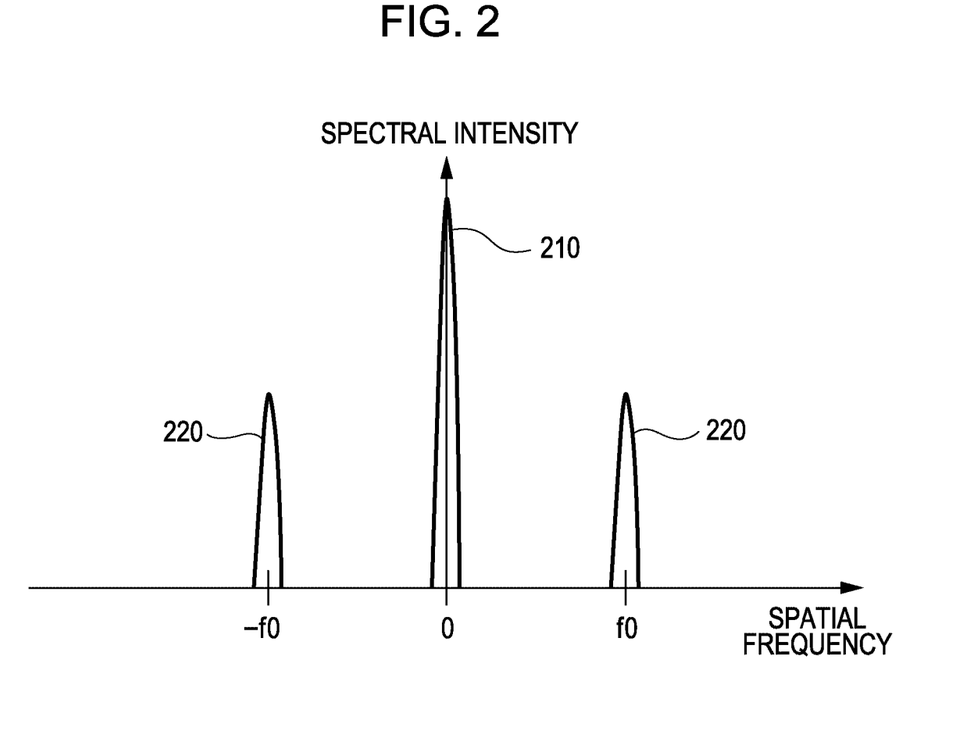
FIG. 2 is a conceptual diagram of a Fourier image.

In equation (6), "$G(f_x,f_y)$", "$A(f_x-f_0,f_y)$", and "$C(f_x,f_y)$" are two-dimensional Fourier transforms of "$g(x,y)$", "$a(x,y)$", and "$c(x,y)$", respectively. In addition, "$f_x$" and "$f_y$" represent x and y components, respectively, of a spatial frequency. FIG. 2 is a conceptual diagram of equation (6). A Fourier image is shown in FIG. 2. The central peak 210 of three peaks of the Fourier image derives from "$A(f_x,f_y)$" and includes only information on an absorption. One of the remaining peaks 220 (peaks corresponding to a carrier frequency $f_0$) derives from "$C(f_x,f_y)$" and the other one of the remaining peaks 220 derives from "$C^*(f_x,f_y)$". Both the peaks 220 include information on a phase and information on an absorption.

In step S103, information on a portion near one of the peaks corresponding to the carrier frequency is extracted and moved to the origin in a frequency space, and an inverse Fourier transform is performed. By the processing of step S103, information containing both the information on the phase and the information on the absorption can be acquired.

In equation (6), "$G(f_x,f_y)$", "$A(f_x,f_y)$", and "$C(f_x,f_y)$" are two-dimensional Fourier transforms of "$g(x,y)$", "$a(x,y)$", and "$c(x,y)$", respectively. In addition, "$f_x$" and "$f_y$" represent x and y components, respectively, of a spatial frequency. FIG. 2 is a conceptual diagram of equation (6). A Fourier image is shown in FIG. 2. The central peak 210 of three peaks of the Fourier image derives from "$A(f_x,f_y)$" and includes only information on the absorption. One of the remaining peaks 220 (peaks corresponding to a carrier frequency $f_o$) derives from "$C(f_x,f_y)$" and the other one of the remaining peaks 220 derives from "$C^*(f_x,f_y)$". Both the peaks 220 include information on a phase and information on the absorption.

In step S103, information on a portion near one of the peaks corresponding to the carrier frequency is extracted and moved to the origin in a frequency space, and an inverse Fourier transform is performed. By the processing of step S103, information containing both the information on the phase and the information on the absorption can be acquired.

Note that in the analysis method according to an aspect of the present invention, information on a phase and information on absorption may be acquired using fringe scanning or the like, instead of the above-described Fourier transform.

In step S104, first phase information $V(x,y)$ is obtained from the information acquired in step S103. "Phase information" represents a parameter indicating a phase changed in accordance with a difference in refractive indices when radiation rays pass through a detected object.

In step S105, information on an absorption intensity gradient is obtained from the information acquired in step S103. It is desirable that the absorption intensity gradient distribution be obtained as information on an absorption intensity gradient. However, any type of information may be obtained as long as it identifies a portion (an edge portion or the like of a detected object) exhibiting an absorption intensity gradient greater than a predetermined value or a portion exhibiting an absorption intensity gradient smaller than the predetermined value. Hereinafter, a case where information on an absorption intensity gradient is the distribution of absorption intensity gradients $\psi(x,y)$ will be explained.

Here, the distribution of absorption intensity gradients $\psi(x,y)$ can be generated from the information acquired in step S103 by extracting the central peak 210 of the Fourier image. However, it is desirable that the distribution of absorption intensity gradients $\psi(x,y)$ be generated from the same peak as that obtained in order to acquire the first phase information. This is because information on the absorption and information on a phase obtained from the same peak are highly correlated with each other and a reconstructed phase image with less distortion can be acquired in the unwrapping process using a weighting function, which will be described later.

Here, the first phase information $\phi'(x,y)$ acquired in step S104 is wrapped into the range of $2\pi$. The state being wrapped into the range of $2\pi$ represents a state being convoluted into the range of $2\pi$, that is, for example, a range from 0 to $2\pi$ or a range from $-\pi$ to $\pi$. Thus, it is necessary to acquire the true phase $\phi(x,y)$, which is not wrapped, from the wrapped first phase information $\phi'(x,y)$. Calculation performed in order to transform wrapped phase information into unwrapped phase information as described above may be called unwrapping (hereinafter, referred to as "unwrapping").

The true phase $\phi(x,y)$ is obtained by establishing four equations (7) to (10) (see Non-Patent Citation 1):

$$\varphi'_{i,j}(x, y) = \varphi_{i,j}(x, y) + 2\pi n_{i,j}(x, y) \tag{7}$$

$$\varepsilon^2 = \sum_{i,j} U(i, j)(\varphi_{i+1,j} - \varphi_{i,j} - \Delta^x_{i,j})^2 + \sum_{i,j} V(i, j)(\varphi_{i,j+1} - \varphi_{i,j} - \Delta^y_{i,j})^2 \tag{8}$$

$$\Delta^x_{i,j} = W\{\varphi'_{i+1,j} - \varphi'_{i,j}\} \tag{9}$$

$$\Delta^y_{i,j} = W\{\varphi'_{i,j+1} - \varphi'_{i,j}\}. \tag{10}$$

Specifically, $n(x,y)$ by which $\varepsilon^2$ in equation (8) is minimized when the value $\phi'(x,y)$ acquired in step S104 is substituted for the individual equations is calculated. That is, the least-squares method is performed. Then, by substituting the acquired $n(x,y)$ in equation (7), the true phase $\phi(x,y)$, which is second phase information, is calculated. Here, "$n(x,y)$" represents an integer, "W" represents a wrapping operator, and "U" and "V" represent weighting functions.

Figure 3:
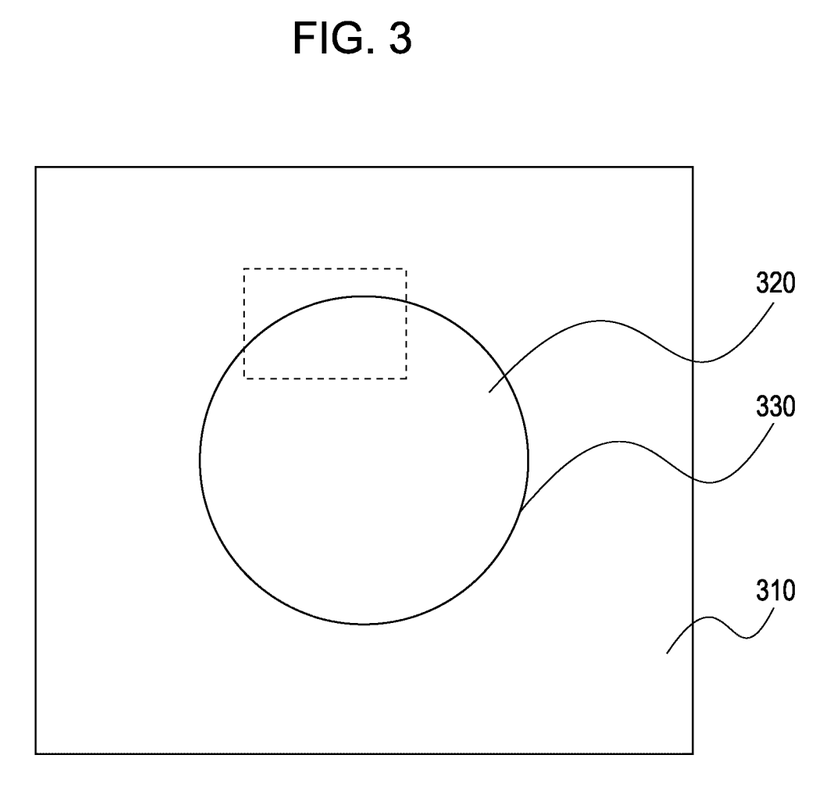
FIG. 3 is an illustration for explaining an edge portion of a detected object.

Here, a problem occurring in an edge portion of a detected object when the wrapped phase information $\phi'(x,y)$ is unwrapped will be explained with reference to FIG. 3. FIG. 3 is a sectional view of a detected object having a cylindrical shape. In FIG. 3, an area 310 not including the detected object, an area 320 occupied by the detected object, and a boundary portion (edge portion) 330 between the areas 310 and 320 are provided.

Since the phase changes in the area 310 not including the detected object and in the area 320 occupied by the detected object are small and smooth, the areas 310 and 320 are detected as portions in which the phase changes continuously. However, since the phase greatly changes in the edge portion 330 of the detected object, the edge portion 330 is detected as a portion in which the wrapped phase changes discontinuously. In the portion in which the phase changes discontinuously, a discrepancy occurs in terms of calculation when unwrapping is performed, and a resultant reconstructed phase image includes distortion.

Meanwhile, in an edge portion of a detected object in which the phase greatly changes, an absorption intensity gradient is large.

Thus, by generating weighting functions U and V that permit discontinuous phase changes and providing the weighting functions U and V for a portion exhibiting a large absorption intensity gradient in absorption intensity gradient distribution when the above-described unwrapping processing is performed, a reconstructed phase image with less distortion can be obtained. That is, for a portion in which the phase changes discontinuously, unwrapping is performed such that the weighting functions U and V are set to values not causing a discrepancy in terms of calculation.

Figure 4:
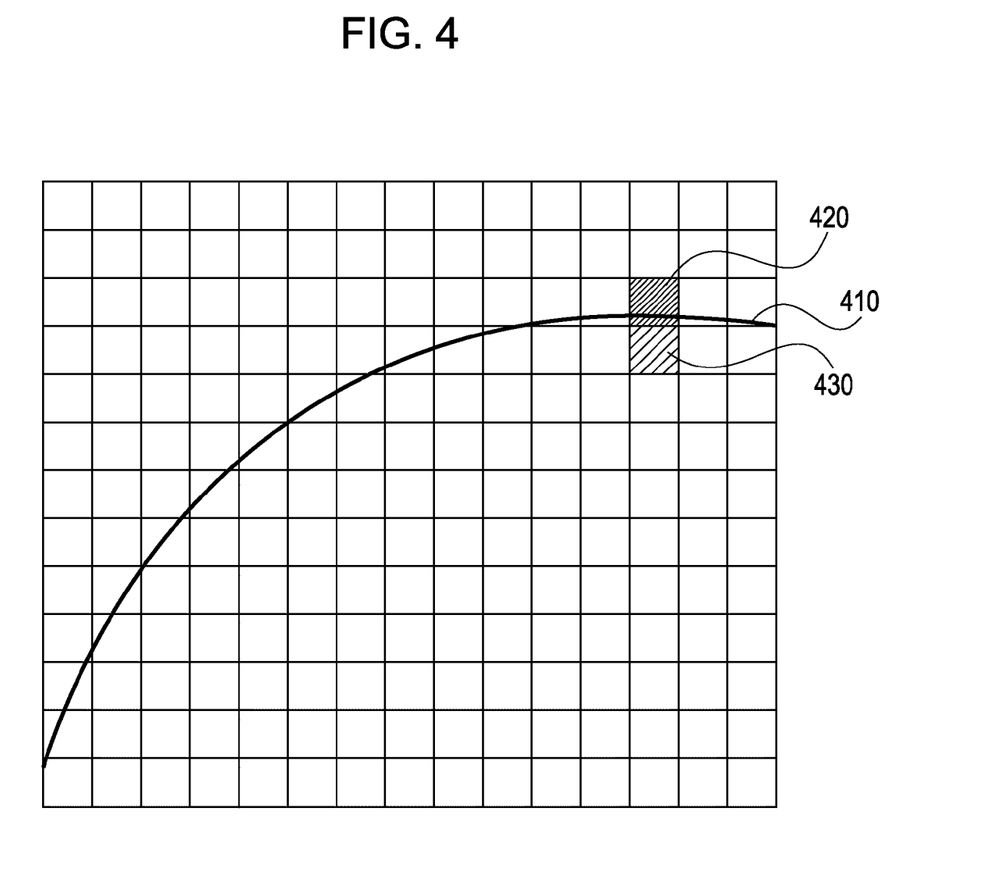
FIG. 4 is an illustration for explaining an example of provision of weighting functions.

A specific method for generating the weighting functions U and V will be explained with reference to FIG. 4. FIG. 4 illustrates absorption intensity gradient distribution in an area surrounded by dotted line in FIG. 3. Referring to FIG. 4, a thick line 410 represents a portion in which the absorption intensity gradient is greater than a predetermined value and corresponds to an edge portion of a detected object.

First, as shown in FIG. 4, absorption intensity gradient distribution is divided into a plurality of pixels. Then, a pixel including an area in which the absolute value of the absorption intensity gradient is greater than a predetermined value is represented by a first pixel 420 and a pixel in which the absolute value of the absorption intensity gradient is smaller than the predetermined value is represented by a second pixel 430. Weighting functions are generated such that different values are provided to the first pixel 420 and the second pixel 430.

An appropriate value between 0 and 1 can be selected as the value of a weighting function in accordance with the shape or the like of a detected object. Here, the "appropriate value" represents a value by which a resultant reconstructed phase image with less distortion can be obtained. For example, in a case where discontinuity in phases is fully permitted, the value of a weighting function can be set to "0". Meanwhile, in a case where phases are not discontinuous, the value of a weighting function can be set to 1 or the like. In addition, an appropriate value can be selected as a predetermined value, which serves as a criterion for determining a weighting function, in such a manner that a resultant reconstructed phase image with less distortion can be obtained. Furthermore, by setting two or more predetermined values, weighting can be performed in a more detailed manner. In addition, the absolute value of an absorption intensity gradient and the value of a weighting function may be set so that they have a one-to-one relationship.

The number of divided pixels is not limited as long as a portion in which an absorption intensity gradient is greater than a predetermined value and a portion in which an absorption intensity gradient is smaller than the predetermined value can be distinguished from each other. In addition, the direction of division, the shape of a pixel, and the like can be set in a desired manner.

As described above, the method according to an aspect of the present invention for generating a weighting function does not need iterative calculations. Thus, compared with the generation method described in Non-Patent Citation 1, a weighting function can be generated quickly and simply.

By substituting the weighting functions generated using the above-described method in equation (8) and performing the above-described unwrapping processing, the true phase φ, which is second phase information, can be obtained (S106).

Then, a reconstructed phase image can be obtained from the second phase information obtained in step S106 (S107).

A radiation imaging apparatus according to an embodiment of the present invention will be explained by taking an X-ray phase imaging apparatus using a Talbot interferometer as an example.

Figure 5:
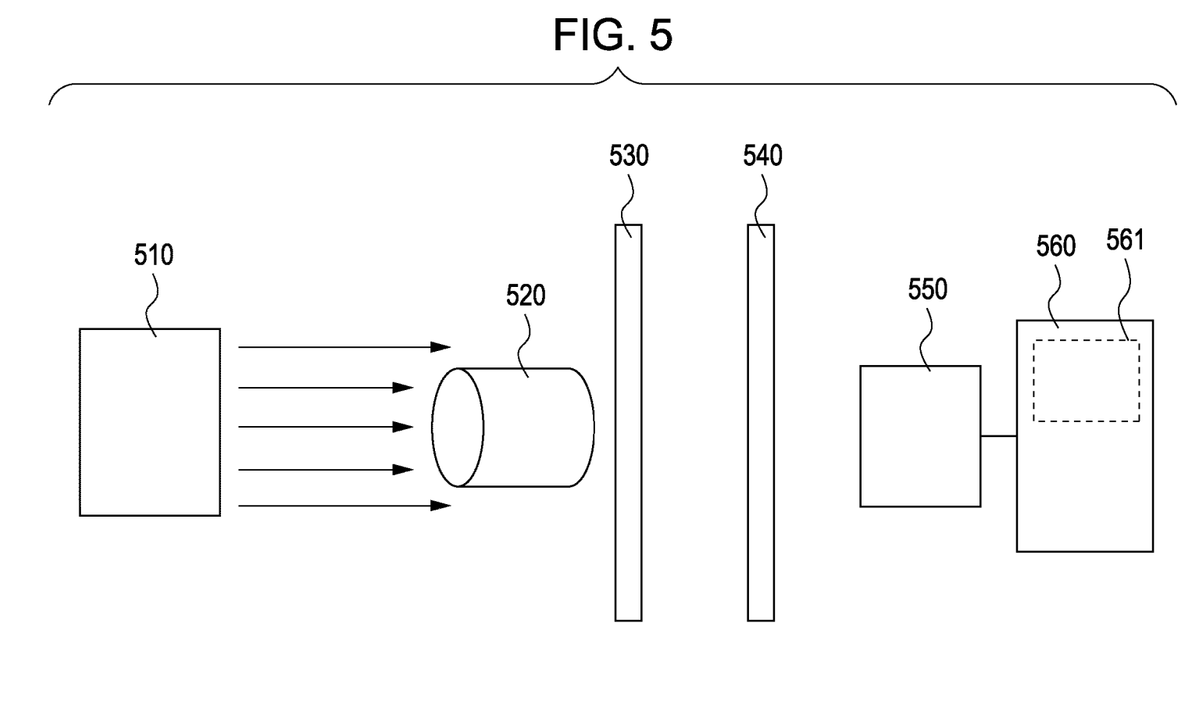
FIG. 5 is an illustration showing an example of the configuration of a radiation imaging apparatus according to an embodiment of the present invention.

FIG. 5 illustrates an example of the configuration of an X-ray phase imaging apparatus using a Talbot interferometer. A flow from generation of X-rays to acquisition of a reconstructed phase image in a case where the X-ray phase imaging apparatus is used will be explained in a specific manner.

First, X-rays generated from an X-ray source 510, which is a radiation generator, pass through a detected object 520. When passing through the detected object 520, a phase change and absorption occur in accordance with the shape or the like of the detected object 520. The X-rays that have passed through the detected object 520 pass through a phase grating 530 and form what is herein termed a "self-image". Here, the "self-image" represents a periodic intensity distribution which reflects the grating pitch of the phase grating 530. X-rays are enhanced when passing through an absorption grating 540 arranged at a position where the self-image is formed. Intensity information of interference fringes of the X-rays that have passed through the absorption grating 540 is detected by a detector 550, which is a detecting unit. The detector 550 is an element capable of detecting intensity information of radiation interference fringes. For example, an imaging element, such as a charge-coupled device (CCD), may be used as the detector 550.

The intensity information of interference fringes detected by the detector 550 is analyzed by an operation unit 560, which performs operations in individual steps in the analysis method described above. The operation unit 560 includes a central processing unit (CPU) 561.

Figure 6:
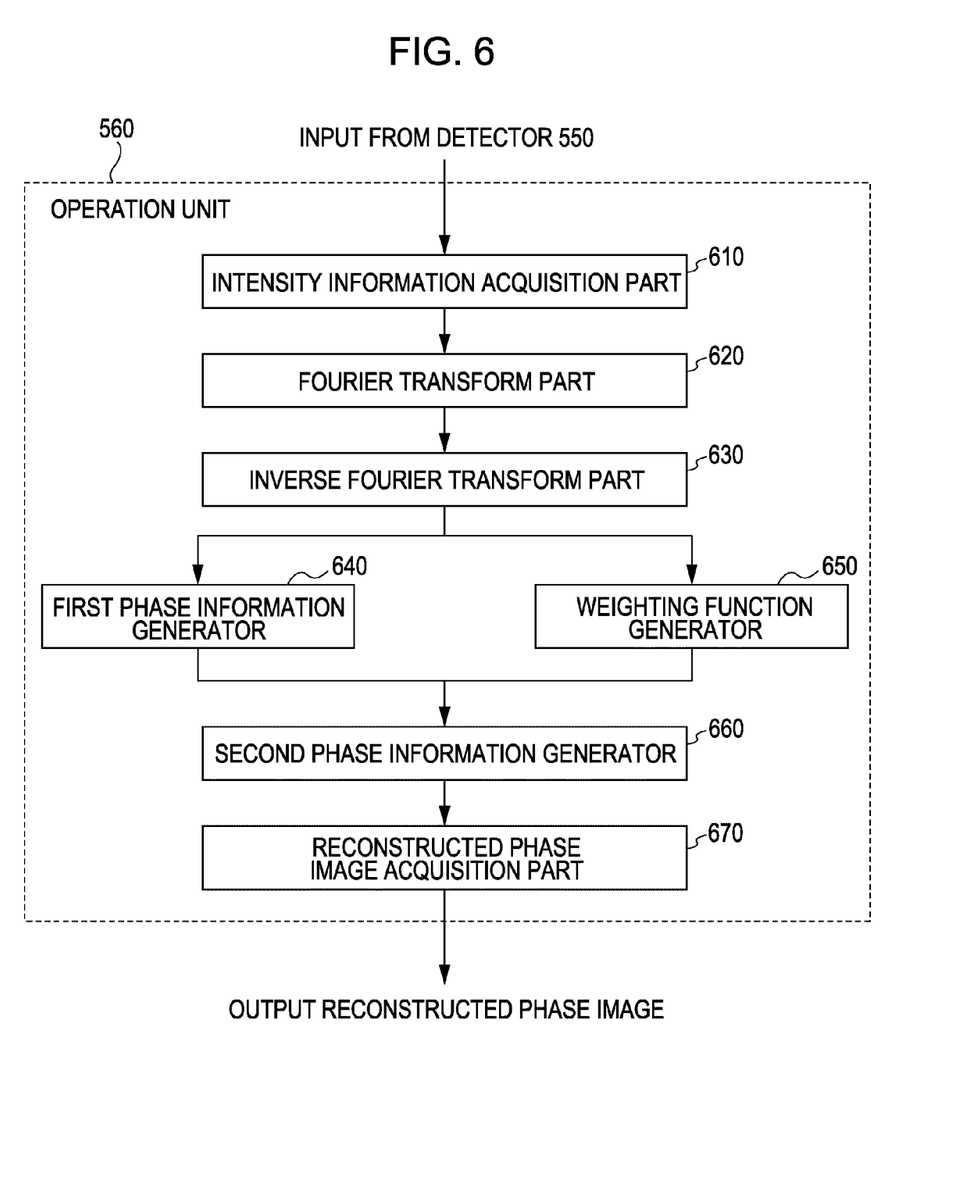
FIG. 6 is an example of a functional block diagram of an operation unit in a radiation imaging apparatus according to an embodiment of the present invention.

FIG. 6 is an example of a functional block diagram of the operation unit 560. An intensity information acquisition part 610 acquires intensity information of interference fringes from data received from the detector 550. A Fourier transform part 620 performs a Fourier transform of the acquired intensity information of interference fringes to obtain a Fourier image. An inverse Fourier transform part 630 extracts information on a portion near a peak corresponding to a carrier frequency in the acquired Fourier image, moves the extracted information to the origin in a frequency space, and performs an inverse Fourier transform. A first phase information generator 640 generates first phase information from the information acquired by the inverse Fourier transform. A weighting function generator 650 acquires absorption intensity gradient distribution from the information acquired by the inverse Fourier transform, and acquires a weighting function on the basis of the absorption intensity gradient distribution. A second phase information generator 660 unwraps the first phase information using the acquired weighting function to generate second phase information. A reconstructed phase image acquisition part 670 acquires a reconstructed phase image from the acquired second phase information.

The operations described above are controlled by a CPU or the like. All the operations may be controlled by a single CPU or a plurality of CPUs. In a case where the same CPU controls the operation performed by the first phase information generator 640 and the operation performed by the weighting function generator 650, the operation unit 560 may include a memory or the like in which the operation result or the like of an operation performed earlier is stored. In addition, the operation unit 560 may include a storage part such as a hard disk, as well as a CPU and a memory or the like.

A radiation imaging apparatus according to an aspect of the present invention may use a crystal interferometer, instead of a Talbot interferometer, as a device configured to produce radiation interference fringes. In addition, when a Talbot interferometer is used, in a case where the resolution of the detector 550 is high, the absorption grating 540 is not necessarily provided.

Although the case where a detected object is located between the X-ray source 510 and the phase grating 530 has been explained above, the detected object may be located between the phase grating 530 and the absorption grating 540.

In addition, a radiation imaging apparatus according to an aspect of the present invention may include an output unit configured to output an obtained reconstructed phase image. The output unit includes, for example, a display configured to display the reconstructed phase image on a screen, a printer configured to print the reconstructed phase image on a paper medium or a film, and the like. The radiation imaging apparatus may also include a recording unit in which the acquired reconstructed phase image is recorded or a storage unit in which the reconstructed phase image is stored. The recording unit is, for example, a recording unit configured to record an image on a compact disc (CD) or the like. The storage unit is, for example, a hard disk.

An example of an analysis program according to an embodiment of the present invention will be explained.

The analysis program is capable of allowing an operation unit such as a CPU to execute individual steps in the analysis method described above. For example, a recording medium in which code of the analysis program is recorded is supplied to a computer or the like, and a CPU, a microprocessing unit (MPU), or the like of the computer or the like reads the code of the program stored in a storage medium to execute the program.

EXAMPLE

An example of the present invention will be explained. In this example, a case where calculation was performed using the analysis method described above for an X-ray phase imaging apparatus using the Talbot interferometer described above will be explained. The parameters described below were used.

Figure 7:
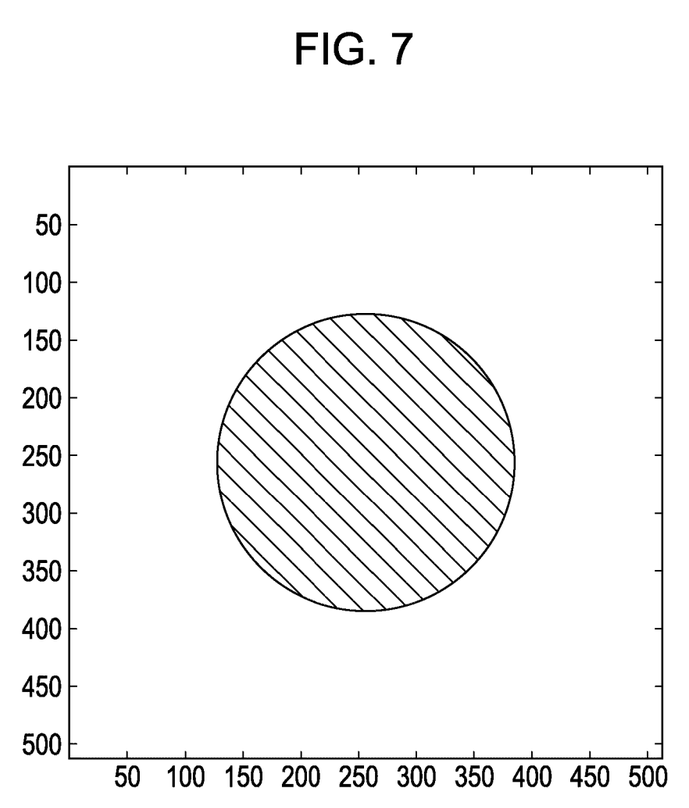
FIG. 7 is a sectional view of a detected object used in an embodiment of the present invention.

Coherent hard X-rays having a wavelength of 0.7 Å at 17.7 keV was used. A silicone object having a cylindrical shape with a diameter of 0.256 mm and a height of 0.1 mm was used as an object to be detected. FIG. 7 is a sectional view of the cylindrical silicone object. X-rays were applied to the cylindrical silicone object in parallel to the central axis of the cylinder (the axis connecting the centers of two circles on the sides of the cylinder). The range for which calculations were performed was a range of 0.512 mm squares, and the center of the square coincided with the central axis of the cylindrical silicone object. A phase grating and an absorption grating having a pitch of 8 µm and generating a phase shift of $\pi$ for each pitch was used. The distance between the phase grating and the absorption grating was set to 11.43 cm, which is the distance at which the first self-image can be obtained by a Talbot interferometer of this device configuration. An image used for calculation had a size of 512 pixels in rows and 512 pixels in columns.

A method according to this example for generating a weighting function will be explained.

Figure 8:
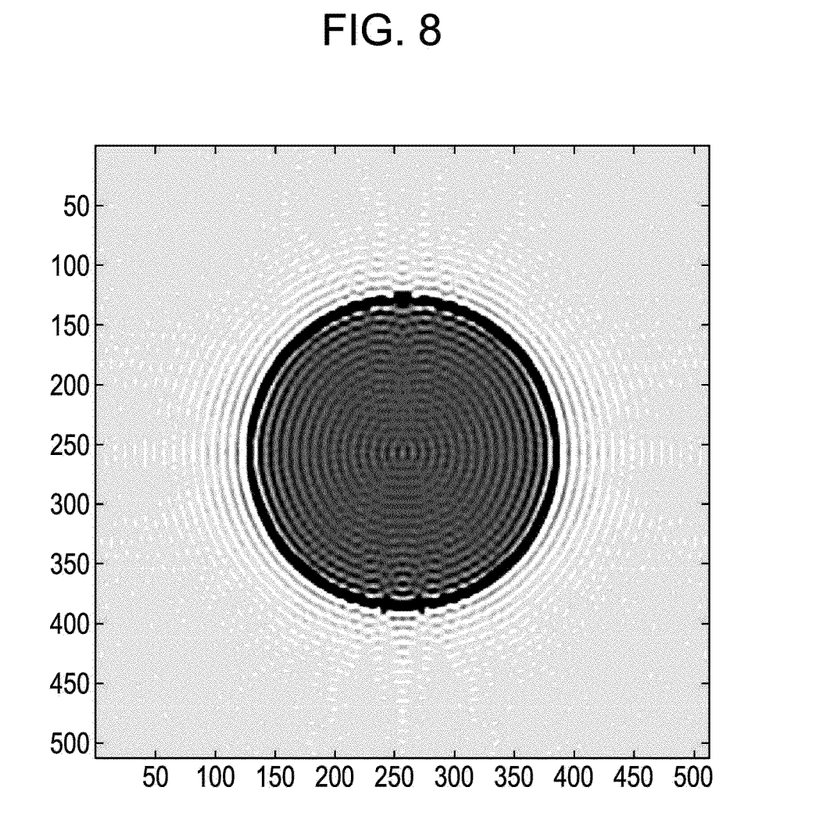
FIG. 8 is an illustration showing absorption intensity gradient distribution of a detected object used in an embodiment of the present invention.

A Fourier transform of intensity information of interference fringes produced under the settings of the parameters described above was performed and a Fourier image was obtained. A peak C $(f_x,f_y)$ (equation (6)) corresponding to a carrier frequency in the obtained Fourier image was extracted and moved to the origin in a frequency space, and an inverse Fourier transform was performed. First phase information $\phi'(x,y)$ was calculated from the argument of an equation obtained by the inverse Fourier transform. Absorption intensity gradient distribution was obtained from the absolute value of the equation obtained by the inverse Fourier transform, and the reciprocal was normalized and defined as a weighting function. FIG. 8 illustrates the obtained absorption intensity gradient distribution. The true phase was obtained using the obtained first phase information and weighting function, and a reconstructed phase image was obtained.

Figure 9:
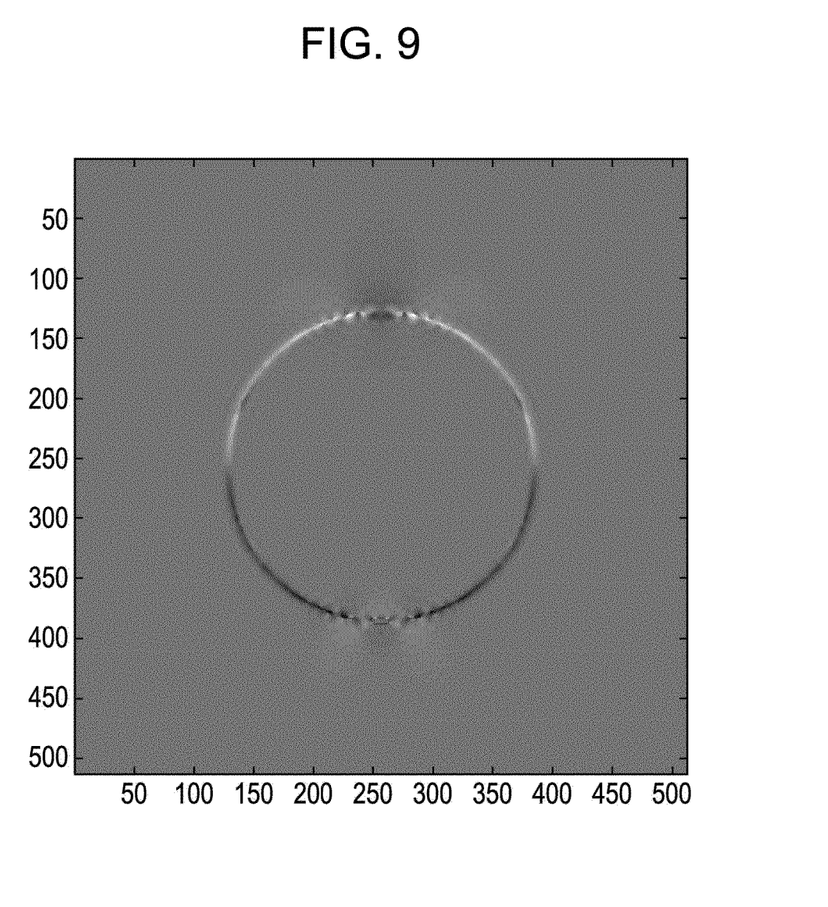
FIG. 9 is an illustration showing a reconstructed phase image of a detected object used in an embodiment of the present invention.

FIG. 9 illustrates the obtained reconstructed phase image. As is clear from the calculation result, a sectional image of a cylinder can be obtained with less distortion.

The time required for generating a weighting function was measured. The calculation conditions were the same as described above. Table 1 shows, for each number of pixels, the time required for generating a weighting function by using a method according to an aspect of the present invention in a case where a single iterative calculation was performed. As a comparative example, the time required for generating a weighting function by using the method disclosed in Non-Patent Citation 1 is also provided. As is clear from Table 1, in the case of all the numbers of pixels, the time required for generating a weighting function by using the method according to the aspect of the present invention is shorter than the time required for generating a weighting function by using the method disclosed in Non-Patent Citation 1.

TABLE 1

| | Number of pixels | | | |
|---|---|---|---|---|
| | 500 × 500 | 1000 × 1000 | 2000 × 2000 | 4000 × 4000 |
| Method disclosed in Non-Patent Citation 1 | 0.11 seconds | 0.45 seconds | 1.81 seconds | 7.55 seconds |
| Method according to an aspect of the present invention | 0.03 seconds | 0.07 seconds | 0.26 seconds | 1.01 seconds |

The time required for obtaining a reconstructed phase image was measured. The calculation conditions were as described above. Table 2 shows the time required for obtaining a reconstructed phase image by using a method according to an aspect of the present invention in a case where the number of iterative calculations is set to 5, 10, 20, and 50. As a comparative example, the time required for obtaining a reconstructed phase image by using a weighting function generated using the method disclosed in Non-Patent Citation 1 is also provided. As is clear from Table 2, the time required for obtaining a reconstructed phase image by using the method according to the aspect of the present invention is shorter than the time required for obtaining a reconstructed phase image by using the method disclosed in Non-Patent Citation 1.

TABLE 2

| | Number of iterative calculations | | | |
|---|---|---|---|---|
| | 5 | 10 | 20 | 50 |
| Method disclosed in Non-Patent Citation 1 | 23.87 seconds | 41.20 seconds | 78.70 seconds | 193.16 seconds |
| Method according to an aspect of the present invention | 18.23 seconds | 32.84 seconds | 61.25 seconds | 147.00 seconds |

In accordance with the above results, in a case where an analysis method according to an aspect of the present invention is used, an accurate weighting function can be generated quickly and simply and unwrapping can be performed quickly compared with a case where the method disclosed in Non-Patent Citation 1 is used. The present invention is not limited to the embodiment described above. Various modifications may be made to the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-278425, filed Oct. 29, 2008, which is hereby incorporated by reference herein in its entirety.

The invention claimed is:

1. A method for acquiring information of a detected object from intensity information of interference fringes of radiation rays that have passed through the detected object, the method comprising the steps of:
   generating first phase information of the detected object wrapped into a range of $2\pi$ from the intensity information of the interference fringes;

generating information on an absorption intensity gradient of the detected object from the intensity information of the interference fringes;

generating a weighting function on the basis of an absolute value of a gradient in the information on the absorption intensity gradient; and generating second phase information by unwrapping the first phase information by using the weighting function.

2. The information-acquiring method according to claim 1, wherein the step of generating the second phase information includes a step of performing a least-squares method.

3. The information-acquiring method according to claim 1, wherein the step of generating the first phase information includes a step of obtaining a Fourier image by performing a Fourier transform of the intensity information of the interference fringes and extracting information on a phase from the Fourier image, and wherein the step of generating the information on the absorption intensity gradient includes a step of extracting information on absorption from the Fourier image.

4. The information-acquiring method according to claim 3, wherein the information on the phase and the information on the absorption are obtained from a peak corresponding to the same carrier frequency in the Fourier image.

5. The information-acquiring method according to claim 1, wherein the information on the absorption intensity gradient is absorption intensity gradient distribution.

6. The information-acquiring method according to claim 5, wherein the weighting function is a function for dividing the absorption intensity gradient distribution into a plurality of pixels including a first pixel including an area in which the absolute value of the absorption intensity gradient is greater than a predetermined value and a second pixel in which the absolute value of the absorption intensity gradient is smaller than the predetermined value and for giving different weights to the first pixel and the second pixel.

7. The information-acquiring method according to claim 6, wherein the weighting function is a function for giving "0" to the first pixel and giving "1" to the second pixel.

8. The information-acquiring method according to claim 1, wherein the radiation rays are X-rays.

9. An apparatus for acquiring information of a detected object, comprising:

a phase grating configured to shift a phase of radiation rays generated by a radiation generator;

an absorption grating configured to absorb a part of radiation rays passed through the phase grating and a detected object;

a detector configured to detect intensity information of interference fringes of the radiation rays that have passed through the absorption grating; and an operation unit configured to acquire phase information of the detected object from the intensity information of the interference fringes detected by the detector, wherein the operation unit performs an operation which includes the steps of generating first phase information of the detected object wrapped into a range of $2\pi$ from the intensity information of the interference fringes, generating information on an absorption intensity gradient of the detected object from the intensity information of the interference fringes, generating a weighting function on the basis of an absolute value of a gradient in the information on the absorption intensity gradient, and generating second phase information by unwrapping the first phase information by using the weighting function.

10. The apparatus according to claim 9, wherein the phase grating is arranged between the detected object and the absorption grating.

11. The apparatus according to claim 9, wherein the operation unit performs the operation which further includes the step of generating an image of the detected object from the second phase information.

12. The apparatus according to claim 9, further comprising a radiation generator configured to irradiate the phase grating with radiation rays.

13. A non-transitory computer-readable medium storing, in executable form, a program for acquiring information of a detected object from intensity information of interference fringes of radiation rays that have passed through the detected object, the program causing a computer to execute processing comprising the steps of:

generating first phase information of the detected object wrapped into a range of $2\pi$ from the intensity information of the interference fringes;

generating information on an absorption intensity gradient of the detected object from the intensity information of the interference fringes;

generating a weighting function on the basis of an absolute value of a gradient in the information on the absorption intensity gradient; and generating second phase information by unwrapping the first phase information by using the weighting function.

14. An operation apparatus that executes the program stored on the non-transitory computer-readable medium according to claim 13.

* * * * *